(12) United States Patent
Takahashi et al.

(10) Patent No.: US 12,343,158 B2
(45) Date of Patent: Jul. 1, 2025

(54) ORAL TOOL

(71) Applicant: Murata Manufacturing Co., Ltd., Nagaokakyo (JP)

(72) Inventors: Tomoki Takahashi, Nagaokakyo (JP); Jun Takagi, Nagaokakyo (JP); Hiroaki Togashi, Nagaokakyo (JP); Hiroki Achiwa, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 970 days.

(21) Appl. No.: 17/328,395

(22) Filed: May 24, 2021

(65) Prior Publication Data

US 2021/0378584 A1 Dec. 9, 2021

(30) Foreign Application Priority Data

Jun. 8, 2020 (JP) ................................ 2020-099288

(51) Int. Cl.
*A61B 5/00* (2006.01)
(52) U.S. Cl.
CPC .......... *A61B 5/4277* (2013.01); *A61B 5/4552* (2013.01); *A61B 5/6843* (2013.01); *A61B 2560/0266* (2013.01); *A61B 2560/0468* (2013.01); *A61B 2562/0247* (2013.01)
(58) Field of Classification Search
None
See application file for complete search history.

(56) References Cited

U.S. PATENT DOCUMENTS

| | | | |
|---|---|---|---|
| 5,957,723 A * | 9/1999 | Gort-Barten | A47J 27/2105 219/247 |
| 8,734,341 B2 | 5/2014 | Howell et al. | |
| 9,968,777 B1 | 5/2018 | Demarest et al. | |
| 10,258,278 B2 | 4/2019 | Howell et al. | |
| 10,602,929 B1 | 3/2020 | McKay | |
| 10,736,612 B2 | 8/2020 | Donovan et al. | |
| 11,013,461 B2 | 5/2021 | Howell et al. | |
| 11,026,664 B1 | 6/2021 | Petrovic | |
| 11,529,093 B2 | 12/2022 | Furukawa et al. | |
| 11,666,278 B1 | 6/2023 | McKay | |
| 11,744,779 B1 | 9/2023 | McGrattan et al. | |
| 2005/0234365 A1 | 10/2005 | Sonis | |
| 2006/0020179 A1 | 1/2006 | Anderson et al. | |
| 2007/0048224 A1 | 3/2007 | Howell et al. | |

(Continued)

FOREIGN PATENT DOCUMENTS

| | | |
|---|---|---|
| CN | 105914694 A | 8/2016 |
| CN | 108720953 A | 11/2018 |

(Continued)

*Primary Examiner* — Jay B Shah
(74) *Attorney, Agent, or Firm* — ArentFox Schiff LLP

(57) ABSTRACT

An oral tool is provided that includes a body and a measurement unit. The measurement unit is disposed in a movable configuration with respect to the body, and includes a sensor unit at an end opposite to an end where the body is disposed. The sensor unit is constructed to be inserted into a mouth. The end of the measurement unit opposite to the end where the sensor unit is disposed is disposed inside the body. The oral tool includes a stress reliever disposed between the measurement unit and the body at a portion where the measurement unit changes a distance from the body while moving.

17 Claims, 6 Drawing Sheets

(56) References Cited

U.S. PATENT DOCUMENTS

| | | |
|---|---|---|
| 2011/0148256 A1* | 6/2011 | Fujimoto ............... H02N 2/186 310/339 |
| 2012/0203128 A1 | 8/2012 | Levison et al. |
| 2012/0289863 A1 | 11/2012 | Goldstein et al. |
| 2013/0006068 A1 | 1/2013 | Gemer et al. |
| 2013/0211270 A1 | 8/2013 | St et al. |
| 2014/0018641 A1 | 1/2014 | Yoshino et al. |
| 2014/0364758 A1 | 12/2014 | Schindhelm et al. |
| 2015/0196251 A1 | 7/2015 | Outwater et al. |
| 2015/0216471 A1 | 8/2015 | Goldstein et al. |
| 2015/0217614 A1 | 8/2015 | Aoki |
| 2015/0306486 A1 | 10/2015 | Logan et al. |
| 2016/0029963 A1 | 2/2016 | Hyde et al. |
| 2016/0120468 A1 | 5/2016 | Mathew et al. |
| 2016/0135728 A1 | 5/2016 | Furukawa et al. |
| 2016/0150981 A1 | 6/2016 | Baker et al. |
| 2016/0150995 A1 | 6/2016 | Ratto et al. |
| 2016/0262694 A1 | 9/2016 | Calcano et al. |
| 2017/0290545 A1 | 10/2017 | Zerick et al. |
| 2017/0347956 A1 | 12/2017 | Zegarelli |
| 2018/0000378 A1 | 1/2018 | Mertio-Oja et al. |
| 2018/0000563 A1 | 1/2018 | Shanjani et al. |
| 2018/0280176 A1 | 10/2018 | Longley et al. |
| 2018/0296442 A1 | 10/2018 | Paz |
| 2019/0183407 A1 | 6/2019 | Furukawa et al. |
| 2019/0192259 A1 | 6/2019 | Kopelman et al. |
| 2019/0246976 A1 | 8/2019 | Howell et al. |
| 2019/0261889 A1 | 8/2019 | White |
| 2020/0163587 A1 | 5/2020 | Bhattacharjee et al. |
| 2020/0303044 A1 | 9/2020 | Stephen |
| 2020/0345536 A1 | 11/2020 | Letizia et al. |
| 2020/0375528 A1 | 12/2020 | Flanagan |
| 2021/0022840 A1 | 1/2021 | Deane et al. |
| 2021/0161633 A1 | 6/2021 | Makin et al. |
| 2021/0204917 A1 | 7/2021 | Wu |
| 2021/0282665 A1 | 9/2021 | White |
| 2021/0307732 A1 | 10/2021 | Farquar et al. |
| 2022/0007961 A1 | 1/2022 | Funch-Nielsen |
| 2022/0008243 A1 | 1/2022 | Osorio et al. |
| 2022/0202169 A1 | 6/2022 | Chan et al. |

FOREIGN PATENT DOCUMENTS

| | | |
|---|---|---|
| JP | S59132115 U | 9/1984 |
| JP | H04136314 U | 12/1992 |
| JP | H07327937 A | 12/1995 |
| JP | H111913 A | 1/1999 |
| JP | 2012075733 A | 4/2012 |
| JP | 2014037844 A | 2/2014 |
| WO | 2004028359 A1 | 4/2004 |
| WO | 2012046567 A1 | 4/2012 |
| WO | 2015125222 A1 | 8/2015 |

\* cited by examiner

ORAL TOOL

CROSS REFERENCE TO RELATED APPLICATIONS

The present application claims priority to Japanese Application No. 2020-099288, filed on Jun. 8, 2020, the entire contents of which are incorporated herein by reference.

FIELD OF THE INVENTION

The present invention relates to an oral tool including a sensor unit that is to be inserted into the mouth or brought into contact with the tongue for measurement of various parameters.

BACKGROUND

Currently, WO 2015/125222, for example, discloses an oral moisture measuring device that detects moisture in the mouth and includes a body, a swing member that swings with respect to the body, a moisture detector disposed at the distal end of the body to detect the moisture by being brought into contact with a measurement target portion in the mouth, and an urging member that urges the swing member.

The current technology has disclosed an oral moisture measuring device including a swing member including a moisture detector, and the swing member configured to swing with respect to the body. As the device is used more times, the housings constituting the body and the swing member collide against each other to deform the device and cause backlash. Thus, the device reduces its measurement accuracy.

SUMMARY OF THE INVENTION

Accordingly, the present invention provides a highly durable oral tool not easily deformed after many times of use.

According to exemplary embodiments, an oral tool is provided that includes a body, and a measurement unit disposed swingably (or movably) with respect to the body and including a sensor unit at an end opposite to an end where the body is disposed. The sensor unit is insertable into the mouth. The end of the measurement unit opposite to the end where the sensor unit is disposed is disposed inside the body. The oral tool includes a stress reliever disposed between the measurement unit and the body at a portion where the measurement unit changes a distance from the body while swinging.

The oral tool according to an exemplary aspect includes the stress reliever disposed between the measurement unit and the body at a portion where the measurement unit changes a distance from the body while swinging. Thus, the oral tool is at least partially prevented from being deformed after many times of use, and is thus highly durable.

Additional features, elements, characteristics and advantages of the exemplary embodiments will become more apparent from the following detailed description of the present invention with reference to the attached drawings.

DETAILED DESCRIPTION OF THE EMBODIMENTS

Figure 1:
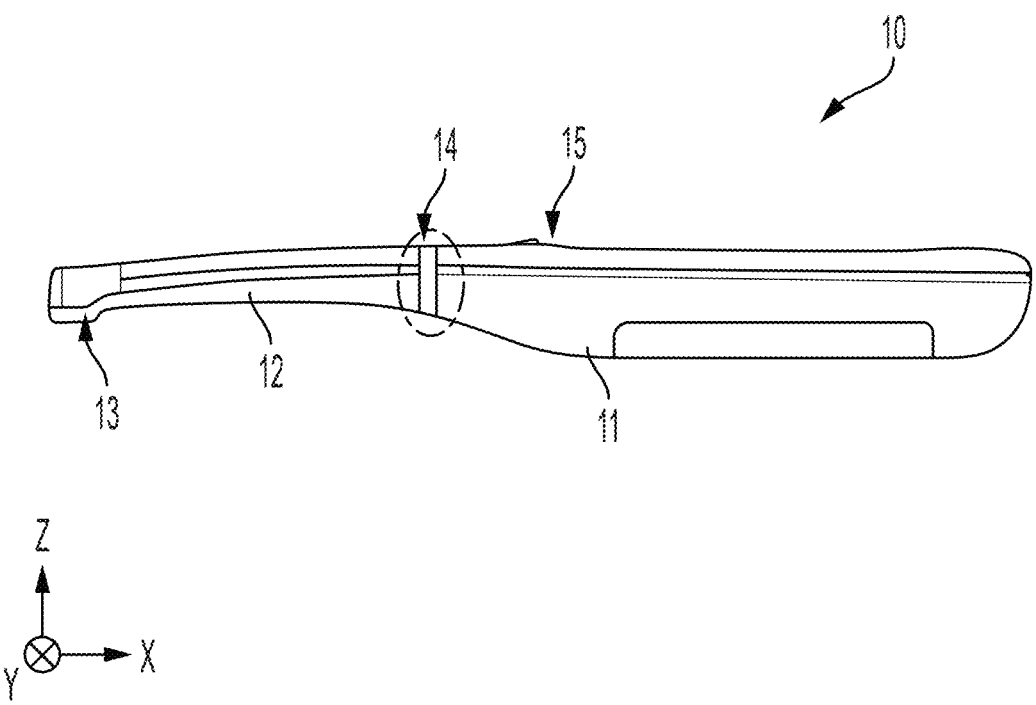
FIG. 1 is a schematic diagram of an oral tool according to a first exemplary embodiment.

An oral tool of a first exemplary aspect includes a body, and a measurement unit disposed swingably with respect to the body and including a sensor unit at an end opposite to an end where the body is disposed. The sensor unit is insertable into the mouth. Moreover, the end of the measurement unit opposite to the end where the sensor unit is disposed is disposed inside the body. The oral tool includes a stress reliever disposed between the measurement unit and the body at a portion where the measurement unit changes a distance from the body while swinging.

This structure at least partially prevents deformation or abrasion caused by swinging and collision of components forming the measurement unit and the body, and thus can keep measurement accuracy.

In an oral tool of a second exemplary aspect, the stress reliever may be disposed at a boundary between the body and the measurement unit.

This structure reduces abrasion resulting from collision of outer covers of the body and the measurement unit at the boundary.

In an oral tool of a third exemplary aspect, the stress reliever can be formed from a material selected from a group consisting of natural rubber, styrene-butadiene rubber (SBR), chloroprene rubber (CR), acrylonitrile rubber (NBR), butyl rubber (IIR), ethylene-propylene rubber (EPDM), silicone rubber, and thermoplastic polyurethane (TPU).

In this structure, the material forming the stress reliever is less likely to hydrolyze, has static physical properties, and thus is durable for long-term use.

In an oral tool of a fourth exemplary aspect, the ratio of the length of the measurement unit to the length of the body in the extension direction in which the measurement unit extends with respect to the stress reliever serving as a boundary may fall within the range of 1:1 to 1:2.

In this structure, the measurement unit is shorter than the body, and thus moves a smaller distance. This structure improves measurement accuracy.

In an oral tool of a fifth exemplary aspect, the measurement unit has a shape that increases a thickness in the extension direction toward the body from the end where the sensor unit is disposed. The ratio of the thickness of the measurement unit where the stress reliever is disposed to the thickness of the stress reliever may fall within the range of 1:1 to 1:2.

In this structure, the distal end is thin to be easily insertable into the mouth. The body is thick to be easily grippable by the hand, and enables uniform application of a load on a measurement target portion without excessively causing stress.

In an oral tool of a sixth exemplary aspect, the stress reliever has a convex shape protruding in a direction in which the measurement unit swings, at the boundary between the body and the measurement unit.

In this structure, the stress reliever with a convex shape in the direction in which the measurement unit swings serves as resistance to at least partially prevent deformation under stress for contracting in the extension direction (x direction) perpendicular to the swing direction, and thus to at least partially prevent excessive deformation and overload on a stopper resulting from the excessive deformation.

An oral tool of a seventh exemplary aspect includes a finger mount that enables gripping of the body, and the stress reliever may be disposed adjacent to the finger mount.

In this structure, the stress reliever is disposed adjacent to the finger mount of the body, and at least partially prevents overload during a measurement.

An oral tool of an eighth exemplary aspect further includes a mechanical switch that switches the sensor unit between a measurement mode and a no-measurement mode.

This structure facilitates a measurement at a specific load using the mechanical switch that starts a measurement upon receiving a specific load, such as in response to a contact with the tongue.

An oral tool of a ninth exemplary aspect includes an elastic member that urges the mechanical switch to the position for the no-measurement mode.

This structure changes the mechanical switch into the no-measurement mode using the elastic member, and control the load on the sensor unit at the distal end of the measurement unit.

An oral tool according to exemplary embodiments will be described below with reference to the attached drawings. Substantially the same components are denoted with the same reference signs throughout the drawings.

First Exemplary Embodiment

Figure 2:
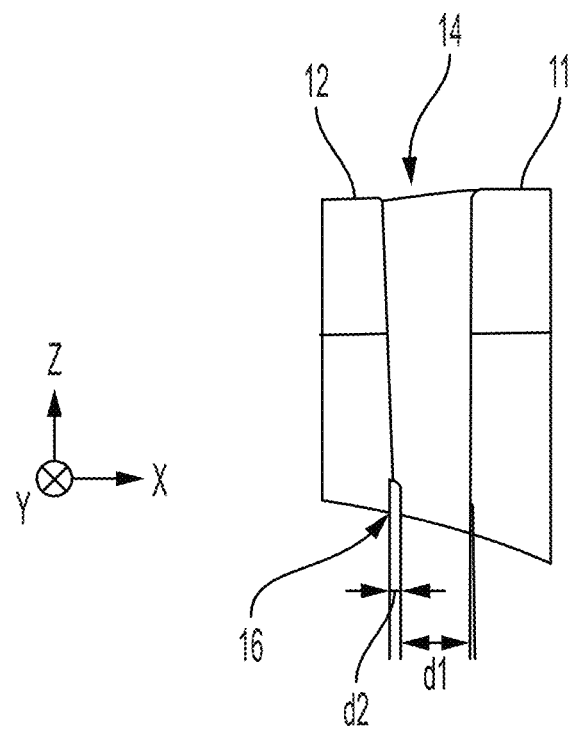
FIG. 2 is an enlarged schematic diagram of a stress reliever disposed at the boundary between a measurement unit and a body.
Figure 3:
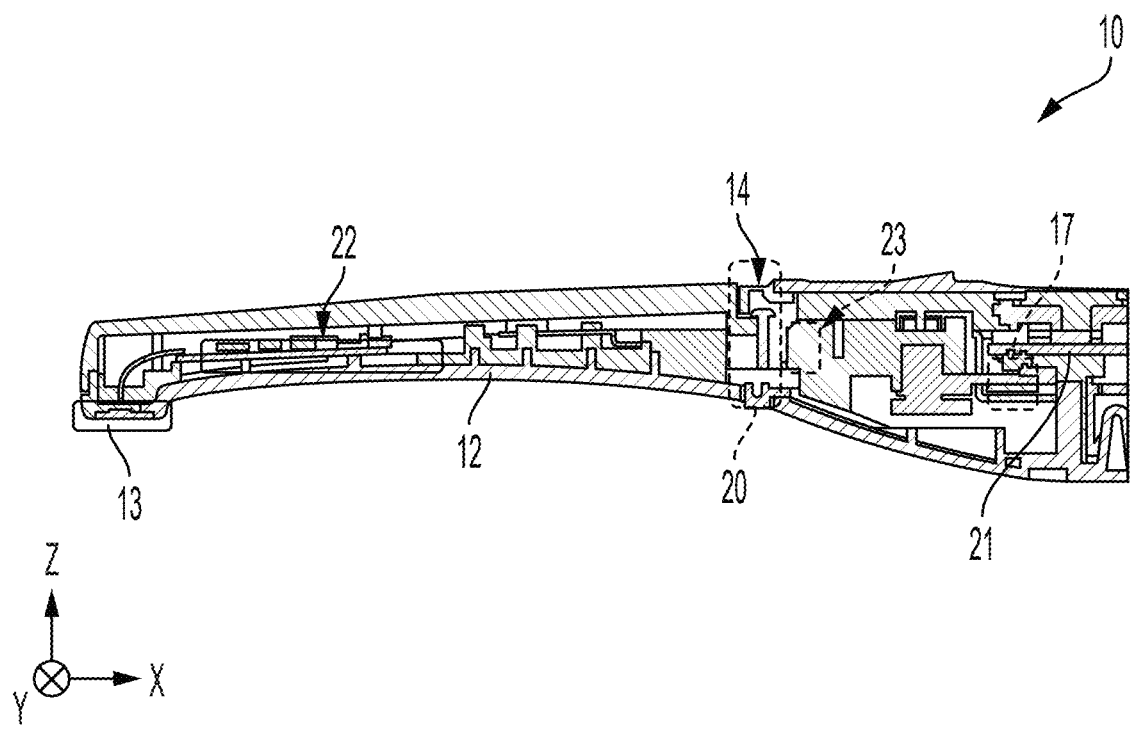
FIG. 3 is a cross-sectional view of the cross-sectional structure including the stress reliever disposed at the boundary between the measurement unit and the body.

FIG. 1 is a schematic diagram of the appearance of an oral tool 10 according to a first exemplary embodiment. FIG. 2 is an enlarged schematic diagram of a stress reliever 14 disposed at the boundary between a measurement unit 12 and a body 11. FIG. 3 is a cross-sectional view of the cross-sectional structure including the stress reliever 14 disposed at the boundary between the measurement unit 12 and the body 11. For convenience, the direction in which the measurement unit 12 extends from the body 11 is denoted with a −x direction, the vertical direction is denoted with a z direction, and the depth direction of the drawing sheet is denoted with a y direction.

The oral tool 10 includes the body 11, the measurement unit 12, and the stress reliever 14. The measurement unit 12 is disposed swingably with respect to the body 11, and includes a sensor unit 13 at an end opposite to an end where the body 11 is disposed. The sensor unit 13 is constructed to be inserted into a mouth (e.g., of a user or patient). The end of the measurement unit 12 opposite to the end where the sensor unit 13 is disposed is disposed inside the body 11. The stress reliever 14 is disposed between the measurement unit 12 and the body 11 at a portion where the measurement unit 12 changes the distance from the body 11 while swinging.

In particular, the stress reliever 14 is disposed between the measurement unit 12 and the body 11. Thus, the oral tool 10 is at least partially prevented from being deformed after many times of use, and thus is highly durable.

Components in the oral tool 10 will now be described.

Body

The body 11 is a member mainly held by the hand. For example, as shown in FIG. 1, the body 11 may include a finger mount 15 on which the finger is placed while being held. As shown in FIG. 3, the body 11 includes a main circuit board 21 that controls measurement of the oral tool 10, and a mechanical switch 17 that switches between a no-measurement mode and a measurement mode. The main circuit board 21 and the mechanical switch 17 are connected to each other. As further illustrated in FIG. 3, the body 11 and the measurement unit 12 are connected to each other at a joint 20 with the stress reliever 14 interposed therebetween. The body 11 may have a length of 5 mm to 20 mm in the x direction.

Measurement Unit

Figure 4:
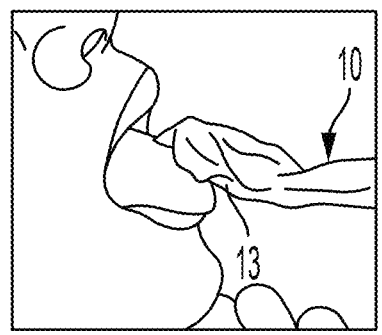
FIG. 4 is a schematic diagram of a sensor unit while being in contact with the tongue.

FIG. 4 is a schematic diagram of the sensor unit 13 brought into contact with the tongue of the mouth.

The measurement unit 12 is disposed swingably with respect to the body 11. For example, as illustrated in FIG. 3, the measurement unit 12 may extend in the −x direction from the body 11, and may be swingable, about a swing rotation shaft 23, in the vertical direction (i.e., the z direction) perpendicular to the x direction or the extension direction, or swingable up and down. Here, the measurement unit 12 swings in a zx plane. Instead of the vertical direction (i.e., the z direction), the swing direction of the measurement unit 12 may be a horizontal direction (i.e., the y direction). While swinging in the horizontal direction, the measurement unit 12 swings in a xy plane.

The measurement unit 12 may have a length of 5 mm to 10 mm in the extension direction (i.e., the x direction).

The measurement unit 12 includes the sensor unit 13 insertable into the mouth at the end opposite to the end where the body 11 is disposed. The measurement unit 12 may include an oscillator circuit board 22 connected to the sensor unit 13. The sensor unit 13 may be, for example, a sensor board for measuring the moisture of the tongue. For example, the sensor unit 13 may be brought into contact with the tongue, and the measurement unit 12 may swing upward (i.e., the z direction).

As illustrated in the cross-sectional view in FIG. 3, the measurement unit 12 may include multiple components including, besides the sensor unit 13 and the swing rotation shaft 23, a lower member being in contact with the mechanical switch 17 on the body 11, and an upper member protecting the components including the oscillator circuit board 22.

The measurement unit 12 has a shape gradually thickened in the extension direction from the end where the sensor unit 13 is disposed toward the body 11. In an exemplary aspect, the ratio of the thickness of the measurement unit 12 where the stress reliever 14 is disposed to the thickness of the stress reliever 14 preferably falls within the range of 1:1 to 1:2. The measurement unit 12 with this shape has a thin distal end to be easily insertable into the mouth. Moreover, the thick body 11 is constructed to be easily grippable by the hand, and enables uniform application of a load on a measurement target without causing excessive stress.

The distal end of the measurement unit 12 including the sensor unit 13 is to be inserted into the mouth, and thus has a thickness of smaller than or equal to 15 mm in the vertical direction.

For example, as shown in FIG. 4, the sensor unit 13 can be configured to start a measurement using the mechanical switch 17 that starts a measurement upon receipt of a specific load, for example, when the sensor unit 13 is brought into contact with the tongue. The mechanical switch 17 may be mechanically pressed in the no-measurement mode or a stand-by state, and may be opened in the measurement mode or a measurement state. The mechanical switch 17 may be pressed and urged by an elastic member such as a spring in the no-measurement mode, and opened with the elastic member such as a spring being pushed upward in the measurement mode. Thus, in response to the pressure from the tongue pressed against the sensor unit 13 exceeding a specific load, the measurement unit 12 levels out to open the mechanical switch 17, and to be ready to start a measurement. Here, the elastic member controls the load that urges the sensor unit 13 at the distal end of the measurement unit 12 downward.

Figure 5A:
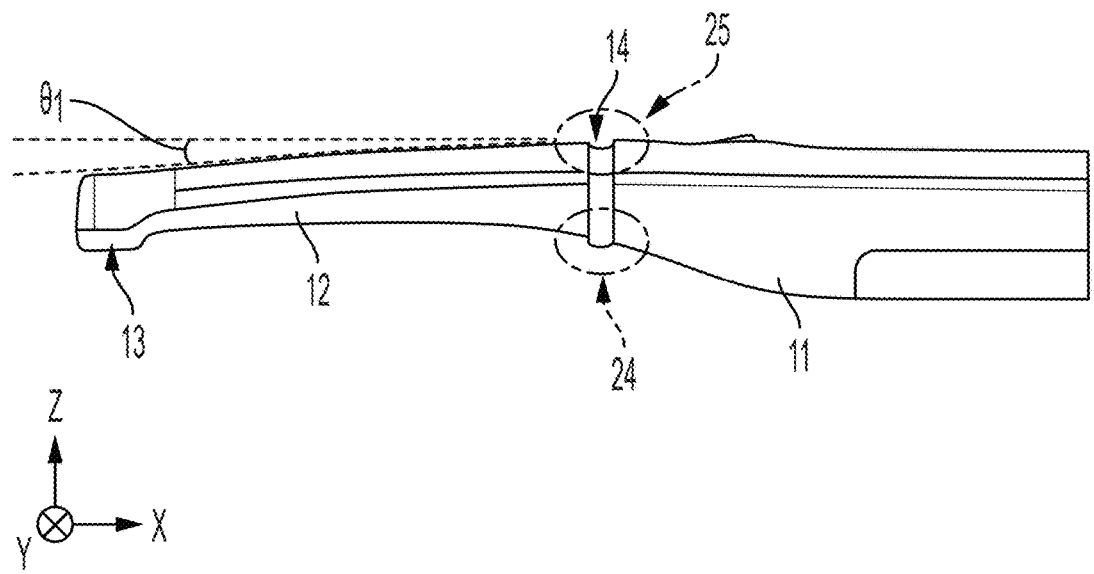
FIG. 5A is a schematic diagram of the vertical position of the stress reliever of the oral tool in a no-measurement mode.

In the no-measurement mode (e.g., a stand-by state) illustrated in FIG. 5A, assuming that the upper surface of the body 11 is a horizontal plane, the distal end of the measurement unit 12 extends at an angle of inclination $\theta_1$ of approximately 3 degrees downward (in the −z direction) with respect to the horizontal plane. On the other hand, in the measurement mode (e.g., a measurement state) illustrated in FIG. 6A, the distal end of the measurement unit 12 extends along the horizontal plane.

In the no-measurement mode, the measurement unit 12 is inclined downward with respect to the horizontal plane. When the sensor unit 13 is brought into contact with the tongue to swing the measurement unit 12 upward (in the z direction), the measurement unit 12 levels out. Thus, the mechanical switch 17 is opened, and the measurement unit 12 enters the measurement mode to start a measurement.

In contrast, the mechanical switch 17 may be opened in the no-measurement mode or the stand-by state, and mechanically pressed in the measurement mode or the measurement state.

Stress Reliever

As illustrated in FIG. 1 and FIG. 2, the stress reliever 14 is disposed at the boundary between the body 11 and the measurement unit 12. For example, the stress reliever 14 may be disposed throughout the boundary between the body 11 and the measurement unit 12. Here, the stress reliever 14 may have an annular shape when viewed in the x direction. A width d1 of the stress reliever 14 at the boundary between the body 11 and the measurement unit 12 is, for example, 2 mm to 20 mm according to an exemplary aspect. This configuration reduces abrasion resulting from collision of outer covers of the body 11 and the measurement unit 12 at the boundary.

As illustrated in FIG. 2, a gap 16 may be left between the measurement unit 12 and the stress reliever 14. The gap 16 has a distance d2 of, for example, 0.05 mm to 5 mm according to an exemplary aspect. The existence of the gap 16 can further reduce the load on the stress reliever when the measurement unit 12 swings.

The stress reliever 14 is a soft member, and in exemplary aspects can be formed from, for example, natural rubber, styrene-butadiene rubber (SBR), chloroprene rubber (CR), acrylonitrile rubber (NBR), butyl rubber (IIR), ethylene-propylene rubber (EPDM), silicone rubber, or thermoplastic polyurethane (TPU) (or called polyurethane rubber (U)). Silicone rubber and thermoplastic polyurethane (TPU) are particularly preferable. These materials are less likely to hydrolyze, have static physical properties, and are thus durable in long-term use.

Figure 5B:
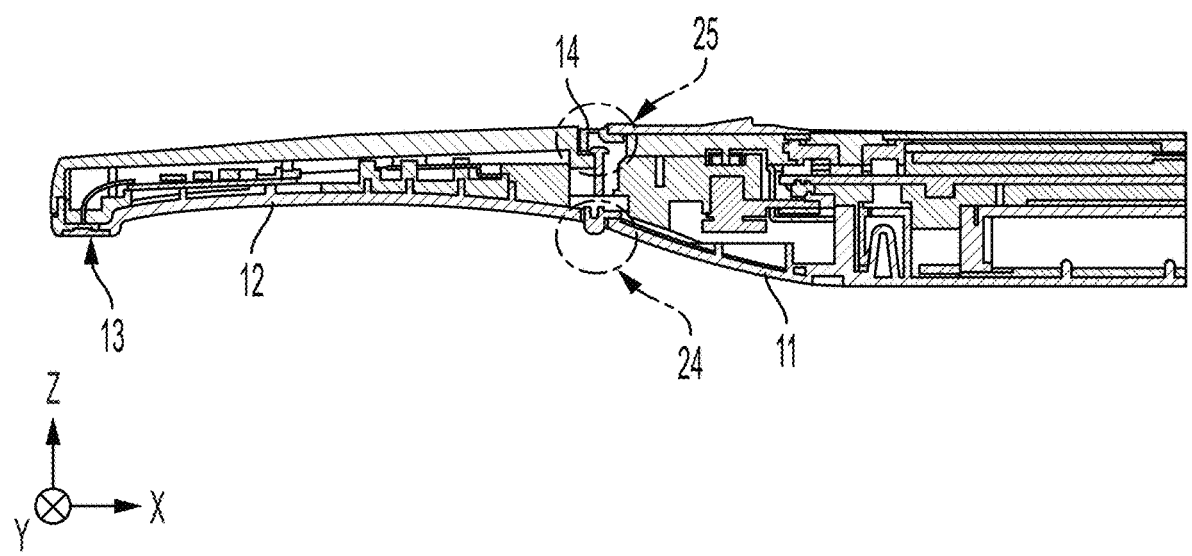
FIG. 5B is a schematic cross-sectional view of the cross-sectional structure of the oral tool in the no-measurement mode shown in FIG. 5A.
Figure 6A:
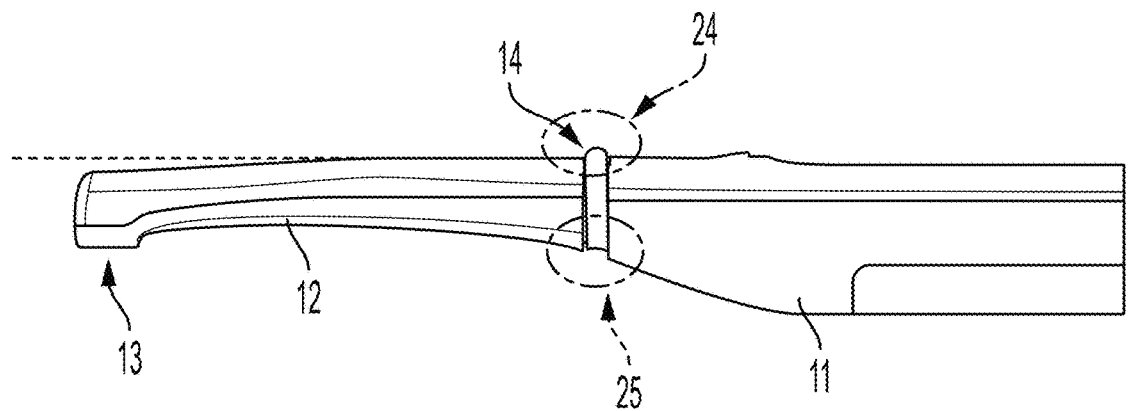
FIG. 6A is a schematic diagram of the vertical position of the stress reliever of the oral tool in a measurement mode.
Figure 6B:
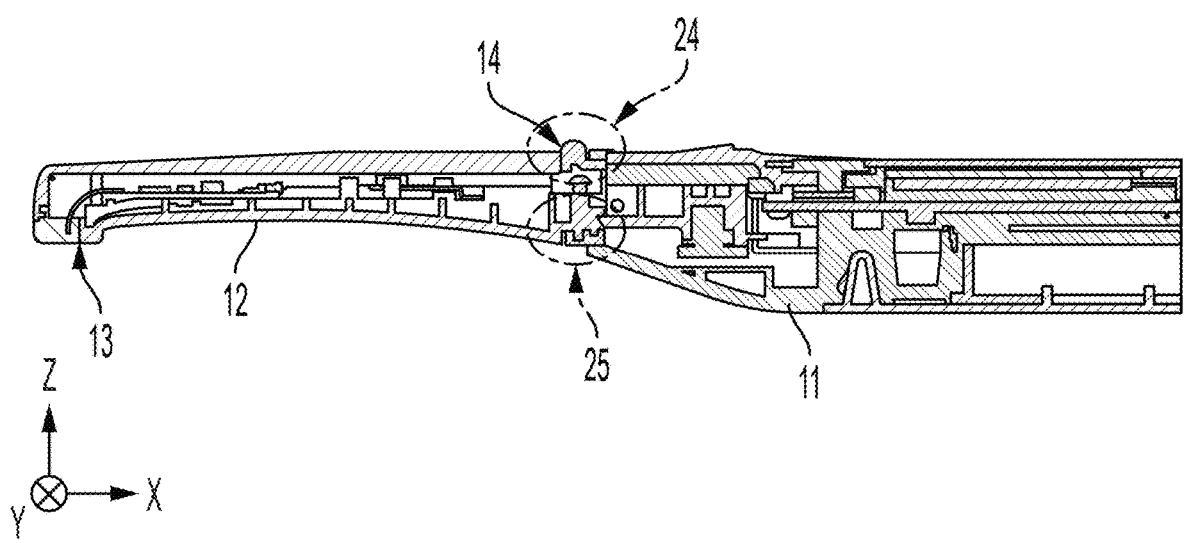
FIG. 6B is a schematic cross-sectional view of a cross-sectional structure of the oral tool in the measurement mode shown in FIG. 6A.

FIG. 5A is a schematic diagram of the vertical position of the stress reliever 14 of the oral tool 10 in the no-measurement mode. FIG. 5B is a schematic cross-sectional view of the cross-sectional structure of the oral tool 10 in a no-measurement mode shown in FIG. 5A. FIG. 6A is a schematic diagram of the vertical position of the stress reliever 14 in the oral tool 10 in a measurement mode. FIG. 6B is a schematic cross-sectional view of a cross-sectional structure of the oral tool 10 in the measurement mode shown in FIG. 6A.

In the no-measurement mode, the measurement unit 12 is held while being inclined downward. As illustrated in FIG. 5A and FIG. 5B, in the no-measurement mode, the stress reliever 14 at the boundary between the body 11 and the measurement unit 12 is pressed by the measurement unit 12 to form a protrusion 24 protruding outward at the lower portion of the boundary. At the upper portion of the boundary, on the other hand, the stress reliever 14 is pulled by the measurement unit 12 to form a recess 25.

In the measurement mode, the measurement unit 12 is horizontally held. As illustrated in FIG. 6A and FIG. 6B, in the measurement mode, the stress reliever 14 at the boundary between the body 11 and the measurement unit 12 is pressed by the measurement unit 12 to form a protrusion 24 protruding outward at the upper portion of the boundary. At the lower portion of the boundary, on the other hand, the stress reliever 14 is pulled by the measurement unit 12 to form a recess 25.

As described above, in either the no-measurement mode or the measurement mode, the stress reliever 14 at the boundary between the body 11 and the measurement unit 12 is deformed to form the protrusion 24 or the recess 25 and reduce the stress.

Stopper

As described above, the measurement unit 12 swings vertically about the rotation shaft 23. On the other hand, as shown in FIG. 3, for example, the joint 20 at the boundary between the body 11 and the measurement unit 12 and the surroundings of the mechanical switch 17 is constructed to function as a stopper mechanism that reduces the swing of the measurement unit 12. In a structure including only the stopper mechanism, the stopper mechanism is deformed due to abrasion or stress with an increase in times of use, to cause backlash and reduce measurement accuracy.

As described above, the oral tool 10 according to the first exemplary embodiment includes the stress reliever 14 at a portion where the measurement unit 12 changes the distance from the body 11 while swinging. Thus, the stress caused during use is reduced by deformation of the stress reliever 14. Thus, the stopper mechanism is prevented from receiving excessive stress, and thus is prevented from being abraded, broken, or deteriorated. This structure is configured to reduce collision between resin components and stress exerted on the stopper, and can be at least partially prevented from being deformed, to thus prevent backlash in the device and deterioration in measurement accuracy.

Ratio in Length Between Body and Measurement Unit

Figure 7:
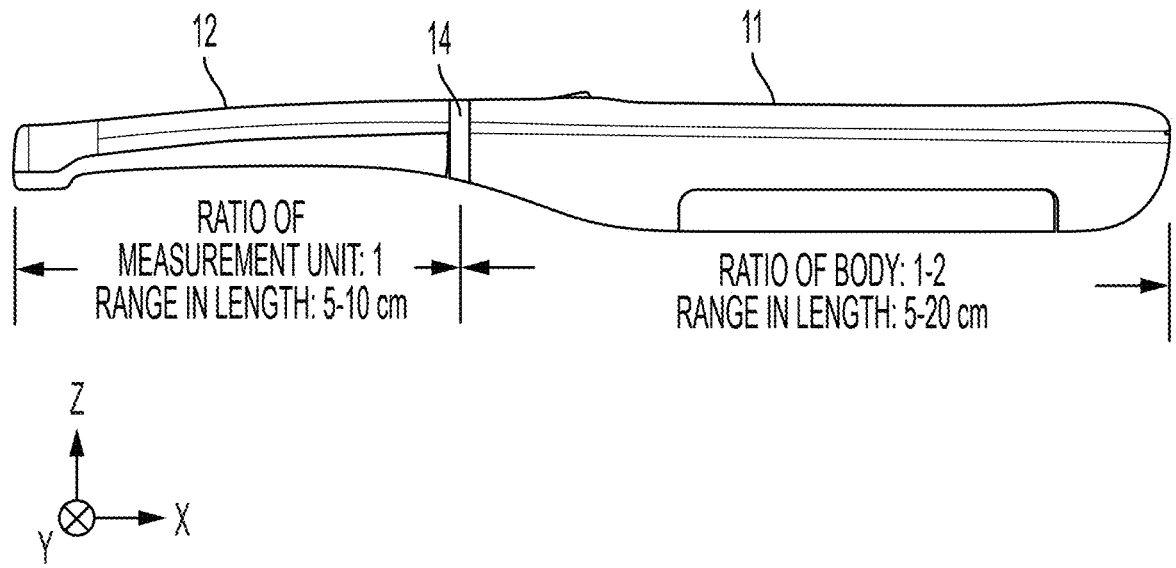
FIG. 7 is a schematic diagram showing the relationship in the longitudinal direction between the length of the measurement unit and the length of the body with respect to the stress reliever serving as a boundary.

FIG. 7 is a schematic diagram showing the relationship in the longitudinal direction (i.e., in the x direction) between the length of the measurement unit 12 and the length of the body 11 with the stress reliever 14 serving as a boundary.

As illustrated in FIG. 7, when the measurement unit 12 has a length of 1, the length of the body 11 falls, for example, within the range of 1 to 2. Specifically, when the ratio in length of the measurement unit to the body falls within the range of 1:1 to 1:2, the measurement unit 12 is shorter than or equal to the body 11. Thus, the distance by which the measurement unit 12 moves can be reduced, so that the measurement is facilitated, and the measurement accuracy can be improved. The measurement unit 12 having the above ratio in length is easily holdable.

Longitudinal Ribs at Joint

Figure 8:
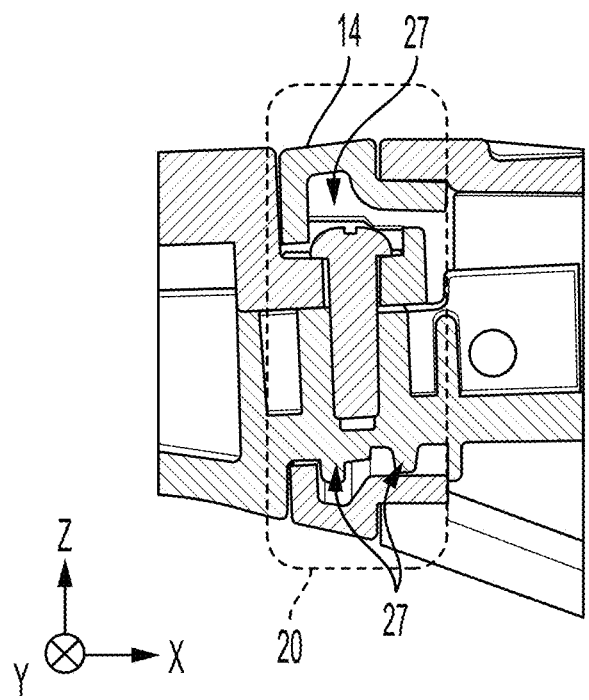
FIG. 8 is a cross-sectional view of longitudinal ribs in the cross-sectional structure at a joint.

FIG. 8 is a cross-sectional view of longitudinal ribs 27 in the cross-sectional structure at the joint 20.

In the oral tool 10, the joint 20 at the boundary between the body 11 and the measurement unit 12 can include, for example, the longitudinal ribs 27 disposed adjacent to the stress reliever 14 and having a shape protruding in the direction (i.e., in the z direction) in which the measurement unit 12 swings. The measurement unit 12 or the body 11 adjacent to the stress reliever 14 including the longitudinal ribs 27 protruding in the swing direction acts against the stress for contracting in the horizontal direction (i.e., in the x direction). In addition, the longitudinal ribs 27 are constructed to prevent warpage of the stress reliever 14 in the annular shape and outward deformation of the stress reliever 14. Moreover, it is noted that the longitudinal ribs 27 can be disposed at either the body 11 or the measurement unit 12 at the joint 20.

Finger Mount

Figure 9A:
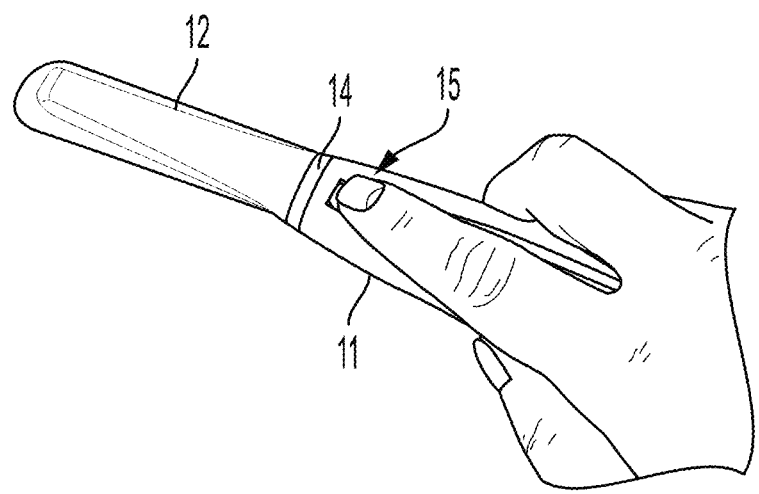
FIG. 9A is a schematic diagram of the oral tool according to the first exemplary embodiment held with the finger being placed on a finger mount of a body.
Figure 9B:
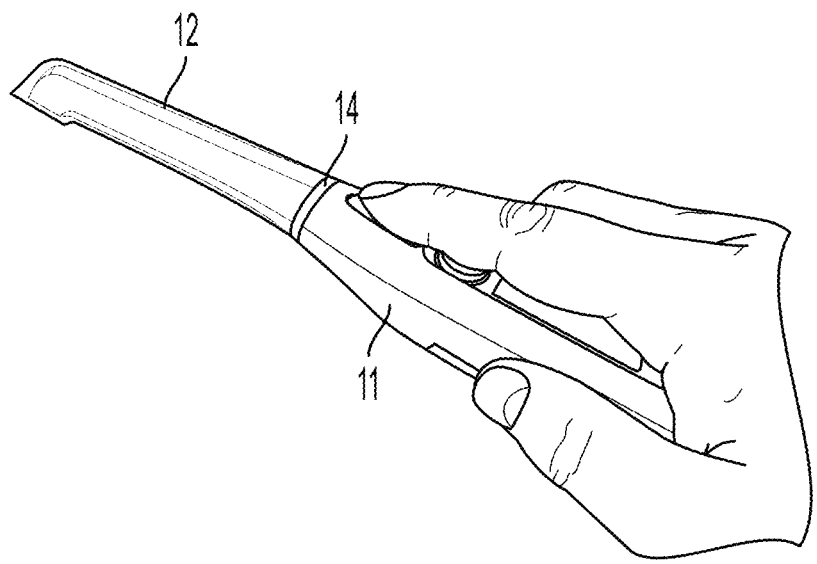
FIG. 9B is a perspective view of the oral tool shown in FIG. 9A, viewed in an oblique direction.

FIG. 9A is a schematic diagram of the oral tool 10 according to the first exemplary embodiment gripped while the finger is placed on the finger mount 15 of the body 11. FIG. 9B is a perspective view of the oral tool 10 shown in FIG. 9A, viewed in an oblique direction.

The oral tool 10 is stably grippable with the finger being placed on the finger mount 15 of the body 11.

Moreover, the stress reliever 14 can be disposed adjacent to the finger mount 15. Thus, overload during a measurement can be at least partially prevented.

In general, it is noted that the present disclosure includes appropriate combinations of any two or more of the above-described exemplary aspects or examples, and can achieve effects of the respective embodiments or examples.

An oral tool according to exemplary embodiments includes a stress reliever between a measurement unit and a body at a portion where the measurement unit changes a distance from the body while swinging. Thus, the oral tool is less easily deformed with an increase of use, and is thus highly durable. This oral tool is thus useful as a medical device.

While the exemplary embodiments of the invention have been described above, it is to be understood that variations and modifications will be apparent to those skilled in the art without departing from the scope and spirit of the invention.

What is claimed:

1. An oral tool, comprising:
   a body;
   a measurement unit connected to the body and including a sensor disposed at an end opposite to an end where the measurement unit is connected to the body, with the measurement unit connected to the body and movable relative to the body where the measurement unit connects to the body; and
   a stress reliever disposed at a boundary between the measurement unit and the body at a position where the measurement unit changes a distance from the body when the measurement unit moves relative to the body,
   wherein the end of the measurement unit connected to the body is disposed inside the body, and
   wherein the stress reliever is disposed at a position, such that the stress reliever is pressed by the measurement unit when the measurement unit moves relative to the body and the stress reliever is constructed to form a protrusion that protrudes outward at one of an upper portion and a lower portion of the boundary and to further form a recess at the other of the upper portion and lower portion of the boundary.

2. The oral tool according to claim 1, wherein the stress reliever comprises a material selected from a group consisting of natural rubber, styrene-butadiene rubber, chloroprene rubber, acrylonitrile rubber, butyl rubber, ethylene-propylene rubber, silicone rubber, and thermoplastic polyurethane.

3. The oral tool according to claim 1, wherein a ratio of a length of the measurement unit to a length of the body in an extension direction in which the measurement unit extends with respect to the stress reliever serving as the boundary is within a range of 1:1 to 1:2.

4. The oral tool according to claim 1, wherein a shape of the measurement unit increases in thickness in an extension direction toward the body from the end where the sensor is disposed.

5. The oral tool according to claim 4, wherein a ratio of a thickness of the measurement unit where the stress reliever is disposed to a thickness of the stress reliever is within a range of 1:1 to 1:2.

6. The oral tool according to claim 1, wherein the stress reliever comprises a convex shape that protrudes in a movement direction of the measurement unit.

7. The oral tool according to claim 1, further comprising a finger mount constructed to enable a gripping of the body, with the stress reliever being disposed adjacent to the finger mount.

8. The oral tool according to claim 1, further comprising a mechanical switch configured to switch the sensor between a measurement mode and a no-measurement mode.

9. The oral tool according to claim 8, further comprising an elastic member constructed to urge the mechanical switch to a position for the no-measurement mode.

10. The oral tool according to claim 1, wherein the stress reliever comprises an annular shape when viewed in an extension direction of the body.

11. The oral tool according to claim 1, wherein the sensor unit is configured to be inserted into a mouth and the sensor comprises a sensor board configured to measure a moisture in the mouth.

12. An oral tool, comprising:
    a body;
    a measurement unit connected to the body and including
       a sensor disposed at an end opposite to an end where the measurement unit is connected to the body,
    wherein the measurement unit is constructed to move relative to the body,
    wherein a stress reliever is disposed at a boundary between the measurement unit and the body, with the boundary being at a position where the measurement unit moves relative to the body, wherein the stress reliever is pressed by the measurement unit when the measurement unit moves relative to the body, such that the stress reliever at least partially prevents deformation to the oral tool due to a movement operation of the measurement unit, and wherein, when the stress reliever is pressed by the measurement unit, the stress reliever is constructed to form a protrusion that protrudes outward at one of an upper portion and a lower portion of the boundary and to further form a recess at the other of the upper portion and lower portion of the boundary.

13. The oral tool according to claim 12, wherein the end of the measurement unit connected to the body is disposed inside the body.

14. The oral tool according to claim 12, wherein the stress reliever comprises a material selected from a group consisting of natural rubber, styrene-butadiene rubber, chloroprene rubber, acrylonitrile rubber, butyl rubber, ethylene-propylene rubber, silicone rubber, and thermoplastic polyurethane.

15. The oral tool according to claim 12, wherein a ratio of a length of the measurement unit to a length of the body in an extension direction in which the measurement unit extends with respect to the stress reliever serving as the boundary is within a range of 1:1 to 1:2.

16. The oral tool according to claim 12, wherein a shape of the measurement unit increases in thickness in an extension direction toward the body from the end where the sensor is disposed.

17. The oral tool according to claim 16, wherein a ratio of a thickness of the measurement unit where the stress reliever is disposed to a thickness of the stress reliever is within a range of 1:1 to 1:2.

* * * * *